United States Patent [19]

Sawyer et al.

[11] Patent Number: 4,684,364

[45] Date of Patent: Aug. 4, 1987

[54] SAFETY ARRANGEMENT FOR PREVENTING AIR EMBOLISM DURING INTRAVENOUS PROCEDURES

[75] Inventors: Philip N. Sawyer, Brooklyn; Joseph F. Fitzgerald, Queens, both of N.Y.

[73] Assignee: Interface Biomedical Laboratories Corporation, Brooklyn, N.Y.

[21] Appl. No.: 484,205

[22] Filed: Apr. 12, 1983

[51] Int. Cl.⁴ .............................................. A61M 5/00
[52] U.S. Cl. ..................................... 604/123; 604/151; 604/247; 604/250; 128/DIG. 12; 251/5; 137/843
[58] Field of Search ........................................ 604/4-6, 604/34, 118, 122, 123, 124, 151, 152, 153, 246, 247, 250, 256, 280, 283, 323, 905, 9, 10, 30, 65-67, 52; 251/4, 5; 137/843; 128/DIG. 12

[56] References Cited

U.S. PATENT DOCUMENTS

| | | | |
|---|---|---|---|
| 220,559 | 10/1879 | Wilson | 137/843 |
| 3,441,245 | 4/1969 | Holland | 251/5 |
| 3,469,582 | 9/1969 | Jackson | 251/5 |
| 3,543,752 | 12/1970 | Hesse | 604/123 |
| 3,672,372 | 6/1972 | Heinlich | 128/349 R |
| 3,687,365 | 8/1972 | Laessig | 236/99 |
| 3,717,174 | 2/1973 | Dewall | 604/34 |
| 3,967,645 | 7/1976 | Gregory | 137/525.1 |
| 4,062,360 | 12/1977 | Bentley | 128/276 |
| 4,103,689 | 8/1978 | Leighton | 128/350 V |
| 4,111,047 | 9/1978 | Bailey | 137/843 |
| 4,126,132 | 11/1978 | Portner et al. | 604/123 |
| 4,134,402 | 1/1979 | Mahurkar | 128/214 R |
| 4,300,552 | 11/1981 | Cannon | 128/214 E |
| 4,303,100 | 12/1981 | Kalb | 251/5 |
| 4,336,800 | 6/1982 | Giovanni | 604/123 |
| 4,385,631 | 5/1983 | Uthmann | 604/284 |
| 4,496,350 | 1/1985 | Cosentino | 604/175 |
| 4,501,531 | 2/1985 | Bilstad et al. | 604/123 |
| 4,515,589 | 5/1985 | Austin et al. | 604/122 |
| 4,535,818 | 8/1985 | Duncan | 137/846 |

FOREIGN PATENT DOCUMENTS

| | | | |
|---|---|---|---|
| 1052659 | 4/1979 | Canada . | |
| 2513490 | 10/1975 | Fed. Rep. of Germany | 604/5 |
| 1510191 | 5/1978 | United Kingdom . | |
| 509746 | 6/1969 | U.S.S.R. | 137/843 |

*Primary Examiner*—Stephen C. Pellegrino
*Attorney, Agent, or Firm*—Pennie & Edmonds

[57] ABSTRACT

An intravenous system is provided which includes a source of intravenous fluid, a needle or catheter for insertion into the vascular system of a patient, a pump for pumping the intravenous fluid via the needle or catheter into the patient and catheters coupling the pump to the source and to the needle. The pump includes an arrangement to terminate pumping upon an opening upon one of the catheters to ambient atmosphere. A flow control is provided in at least one of the catheters to prevent movement of air through the corresponding catheters into the patient.

30 Claims, 6 Drawing Figures

SAFETY ARRANGEMENT FOR PREVENTING AIR EMBOLISM DURING INTRAVENOUS PROCEDURES

FIELD OF INVENTION

This invention relates to intravenous procedures and more particularly to safety arrangements for preventing the entry of air into patients' vascular systems and causing air embolisms therein. The invention also relates to methods of making safety arrangements for intravenous procedures.

BACKGROUND

Procedures have long been known involving the introduction of fluids into the vascular systems of patients. These have developed to a point of employing a source of fluid for intravenous procedures and connecting such source via a pump through a needle or catheter into the vascular system. The pump itself has been developed to a point that when connecting catheters are accidentally opened to ambient atmosphere, the pumping operation is terminated thereby to reduce the possibilities of air being introduced into the vascular system. This is necessary because the introduction of air will cause an embolism which in turn may be fatal to the patient being treated. Nevertheless, the use of such a pump, which is commercially available, is not always effective to prevent accidents of the aforenoted type in all cases. Thus, for example, when the intravenous tubing is coupled to a catheter on the down stream side of the pump, and this catheter becomes accidentally opened to ambient atmosphere, the pressure differential between ambient atmosphere and the vascular system in which the distal tip of the catheter resides is such as to cause air to be sucked through the catheter into the vascular system. This accidental occurrence has been known to cause serious harm to the patient being treated. A number of patents have been found to deal with intravenous procedures and problems of the aforenoted type, as well as to related systems exposed to pressure differential or the like. These patents include U.S. Pat. Nos. 2,538,662; 3,570,808; 3,595,228; 3,599,670; 3,888,249; 3,906,934; 4,067,329; 4,103,686; 4,252,116; 4,324,239; and 4,335,747.

C. Abbott in Patent 2,538,662 discloses a surgical apparatus for the intravenous administration of liquids, such as whole blood, blood plasma, dextrose solutions, and the like and is directed particularly to an expendible valve unit construction used in such surgical apparatus.

J. Wren, in U.S. Pat. No. 3,570,080, discloses a coupling assembly for releasably attaching an air hose to a regulator of the type used in conjunction with the face mask of an underwater diving apparatus. The coupling is readily detachable and a valve mechanism is provided so that when the air hose is decoupled from the regulator underwater, the valves provided in the regulator air inlet and in the end of the air hose are immediately biased to a closed position. Such a construction and arrangement might have utilization in connection with intravenous procedures.

R. Simon, in Patent 3,595,228, discloses a portable alarm device attached to a coupling in a therapeutic apparatus to provide an alarm to alert hospital personnel under certain dangerous conditions as might apply to a respirator flow line or a tracheostomy tube assembly for indicating a break therebetween.

In U.S. Pat. No. 3,599,670, J. Gurner discloses a fluid coupling with a valve means having such provision that if a maximum rate of flow through a hose is exceeded as, for example, by leakage, the coupling valve will close and prevent further flow.

In U.S. Pat. No. 3,888,249, D. Spencer discloses a catheter for prolonged infusion of medication into an artery. The catheter is provided with a tip design employing a flap valve principle to assure uniform and steady diffusion of the medication into the blood stream and to inhibit retrograde flow of blood into the catheter thereby to minimize clotting and blockage of medication flow.

W. Haverland discloses in Patent 3,906,034 a pressure sensor-timer alarm for pressure sensitive devices wherein a plunger, having a magnetically mounted switch actuator, actuates a switch in response to pressure changes from a diaphragm. A failure to actuate the switch in either phase of the breathing cycle within a preset time causes the actuation of an alarm.

B. Winicki discloses in Patent 4,067,329, a warning device warning of the disconnection of a tube from another tube such as, for example, of a respirator cannula from a patient's medical apparatus.

In Patent 4,103,686, R. LeFevre discloses a dual valve assembly for intravenous infusions from multiple parenteral fluid sources. The assembly controls forward and reverse flow through a flow line and includes normally seated first and second valves mounted for movement toward and away from respective valve seats to control flow in such a manner as to prevent reverse flow through the assembly.

M. Gordon shows in Patent 4,324,239, a safety valve for preventing air embolism and hemorrhage. The safety valve disclosed is useful for catheterization procedures and is characterized by a piston having an internal flow path and so arranged as to be biased to a closed position. The arrangement is such as to prevent air embolism and hemmorhage.

In Patent 4,355,747 is disclosed an arrangement which is effective to exclude air or other undesirable gas in a connecting procedure.

None of the aforegoing patents, nor any of the other arrangements known heretofore, is effective to the same degree as the structure to be described below in the preventing of the introduction of air into the vascular system of a patient.

SUMMARY OF INVENTION

It is an object of the invention to provide an improved arrangement for preventing air embolism or the like in intravenous procedures involving patients into whom are introduced in-dwelling catheters or needles.

It is another object of the invention to provide an improved valve construction.

Yet another object of the invention is to provide improved methods and techniques for the formation of systems allowing the introduction of fluids into patients and the like in such a manner as to prevent the introduction of air upon an opening of the system to ambient atmosphere by accident or otherwise.

In achieving the above and other objects of the invention, there is provided a flow control arrangement comprising input means and output means each provided with a bore constituting a flow channel and further means adapted for providing a connecting channel between the bores in response to positive pressure in one of the bores, and for collapsing and thereby obturating the connecting channel in response to a pressure in one of said bores which is negative relative to ambient atmospheric pressure.

In accordance with a particular preferred arrangement, the input, output and further means mentioned above are parts of a tubular structure, and the tubular structure is monolithic. The tubular structure may preferably be formed of a resilient material and, even more preferably, of a silicone rubber or the like.

In accordance with a feature of the invention, there is provided a clip arrangement which is employed in conjunction with the further means mentioned above to yieldably constrain the same to a flattened shape. A relatively rigid support tube may be provided having spaced ends and being provided with a bore within which the aforesaid tubular structure is partly accommodated. The tubular structure may preferably include end portions extending out of the support tube and being rolled back along the support tube ends for engagement therewith. Preferably, the input and output means taper towards the said further means.

In accordance with a further and more particular aspect of the invention, there is provided a housing provided with first and second channels of different diameters in coaxial relationship to define a shoulder therebetween. The support tube and tubular structure are accommodated in the first channel and a plug means is insertable into the first channel to trap the support tube and tubular structure against the shoulder. In accordance with a specific arrangement, a catheter is accommodated in the second channel. The plug and catheter provide passageways coupled through the aforesaid tubular structure. A needle for insertion into the vascular system may be coupled to the catheter in some instances, but in other instances the catheter itself is introduced into the vascular system.

According to yet another aspect of the invention, an intravenous system is provided comprising a source of intravenous fluid, a needle or catheter for insertion into the vascular system of a patient, a pump for performing a pumping operation and urging the fluid from the source to said catheter, catheters coupling said pump to said source and to said needle, said pump including means to terminate said pumping operation upon an opening of one of said catheters to ambient atmosphere. In conjunction with the foregoing, a flow control means is provided in at least one of the aforesaid catheters to prevent movement of air through the corresponding catheter upon an opening of the latter to ambient atmosphere.

In accordance with yet another aspect of the invention, there is provided a method for making a flow control unit comprising flattening the central portion of a resilient tube by bending the tube over a mandrel and retaining the flattening by applying at least one clip to the thusly flattened portion, straightening the tube and inserting the same into a relatively rigid tube, and rolling back the ends of the resilient tube over the ends of the rigid tube to form a pressure responsive component.

The above and other objects, features and advantages of the invention will be found in the detailed description which follows hereinbelow as illustrated in the accompanying drawing.

DETAILED DESCRIPTION

In intravenous procedures as may be performed in a hospital for the introduction of a fluid into the vascular system of a patient, there has never been developed a monitoring procedure which will reliably prevent the accidental detachment of a catheter. This usually results in turn in the introduction of air into the vascular system thereby causing harmful embolisms which may in fact result in death or injury to the patient being treated.

In intravenous procedures, the pressure differential between ambient atmospheric pressure and the pressure in an in-dwelling tube in the vascular system is normally such as to cause air bubbles to be sucked into the vascular system when the associated catheter is inadvertently opened to air. In some known systems, a commercially available pump (valley lab I.V. 5000B volumetric infusion pump made by Modern Medical Systems, of New Hyde Park, N.Y.) is employed in such a manner that, when the system is opened to ambient atmosphere, the pump terminates its pumping operation. This provision is uniquely important in intravenous procedures, but does not prevent the inadvertent movement of air into the vascular system as may result from the aforenoted pressure differential.

Figure 1:
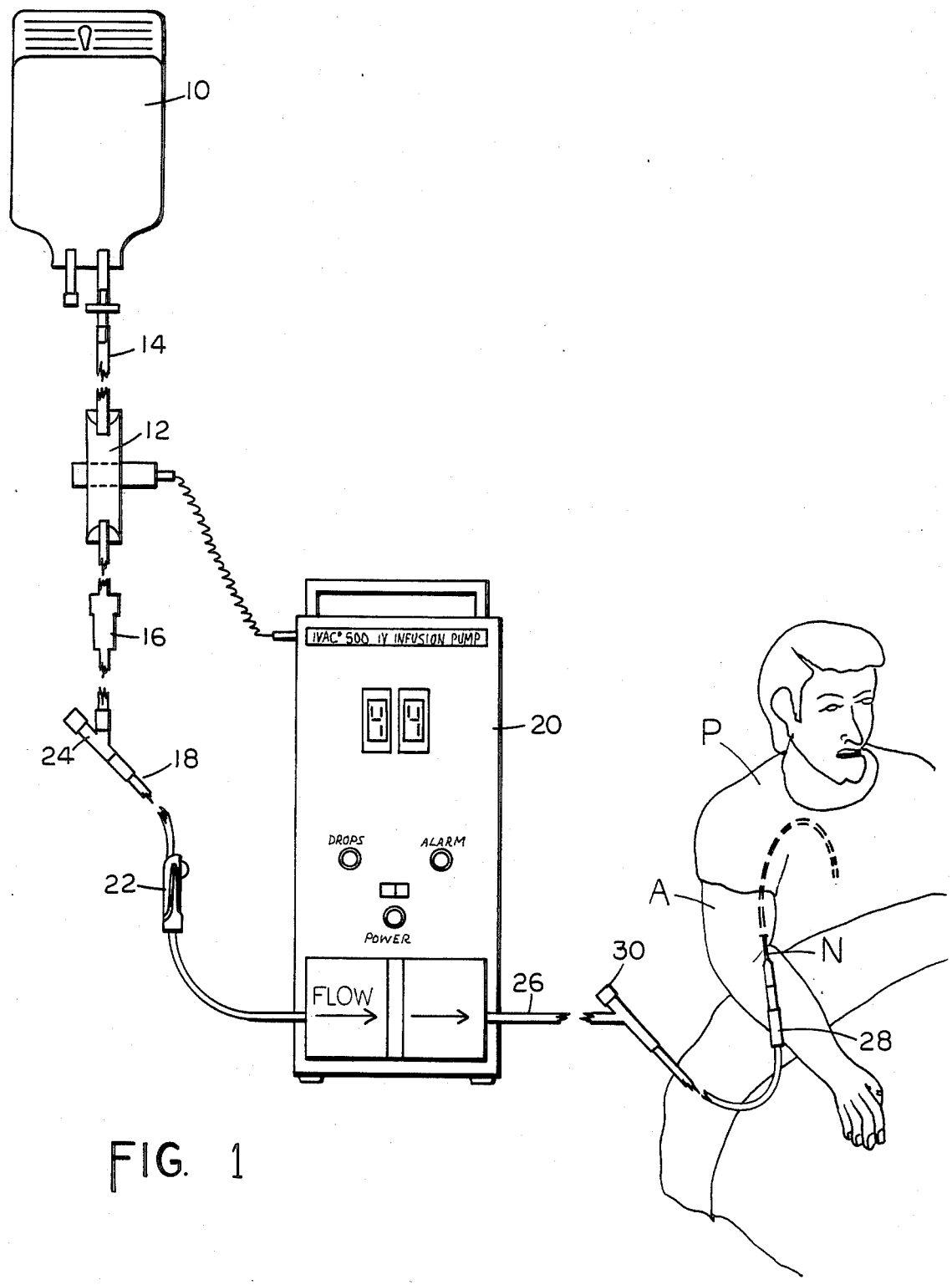
FIG. 1 is a generally pictorial partially broken away view of an intravenous procedure involving a patient and the provisions of the invention.

In FIG. 1 is indicated the physical arrangement necessary for an intravenous procedure as may be performed in a hospital or the like. The patient is indicated generally at P and into the patient's arm A is inserted a needle or catheter N through which the introduction of an intravenous fluid may be effected.

At 10 is indicated a source of intravenous fluid of known type. The source 10 is connected to a reservoir 12 via a catheter 14 with the fluid dripping downwardly drop by drop into the reservoir 12 eventually to be connected via a coupling 16 to a catheter or I.V. tubing 18 feeding into pump 20. A safety arrangement of the invention may be included at 22 if desired. A spur 24 is indicated for the introduction of medical preparations, nutritional perparations or the like according to well known techniques. The pump 20 is of commercially available type which as aforesaid will terminate operation upon an occurrence of a disturbance such as the detachment of the catheter 18 from the coupling 16.

The pump 20 feeds into an intravenous tubing 26 which in turn is connected via a safety arrangement 28 of the invention to the in-dwelling intravenous catheter N. The tubing 26 may also be provided with a spur 30 which enables the introduction of various types of preparations into the fluid flowing to catheter 26 and via catheter or needle N into the vascular system of patient P.

The function of the safety arrangement is to permit the flow of fluid through the I.V. tubing and into the associated catheter under normal conditions wherein the fluid circuit is closed and is not open to ambient atmosphere. A further function is for this safety arrangement to provide a barrier against the penetration of air from the atmosphere due to differential negative pressure between the vascular system and ambient atmosphere as has been found sufficient to cause the sucking of air bubbles into the vascular system thereby to cause embolisms or other harm to the patient being treated.

Figure 2:
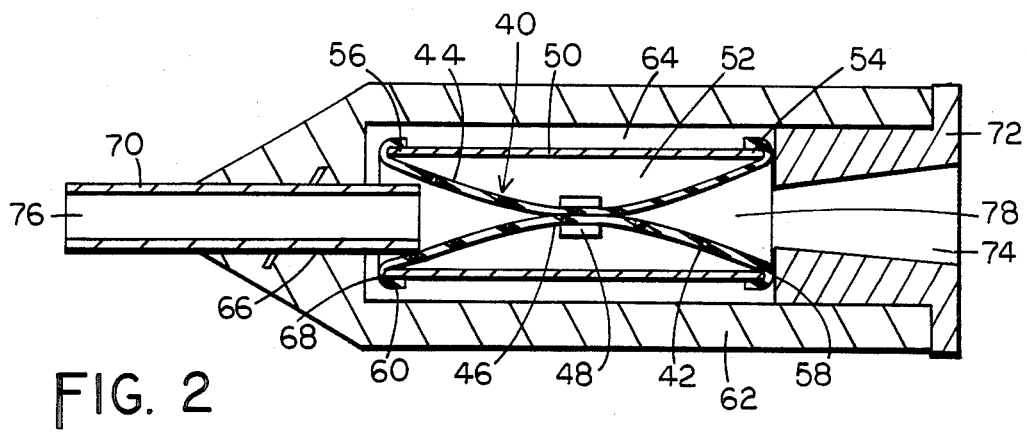
FIG. 2 is an axial section through a flow control valve provided in accordance with a preferred embodiment of the invention.

The structure of the invention includes a resilient tube formed of silicone rubber or the like which is flexible and deformable and readily responsive to the pressures involved in intravenous procedures. This tube is indicated at 40 in FIG. 2. It includes an upstream portion 42, a downstream portion 44 and a central or coupling portion 46. Portions 42 and 44 taper downwardly towards the central coupling portion 46 which is in flattened condition is maintained thusly by a clip arrangement indicated at 48. This clip arrangement may consist of two U-shaped clips which are edge pinching clips applied to the flattened tubing in a manner to be indicated hereinafter in greater detail. These clips may be formed of plastic or the like and are slipped over the flattened central portion 46 to stay in position thereupon to retain this flattened condition. The clips do not engage completely across the flattened portion of the tubing as will be referred to in greater detail hereinbelow.

A support tube 50 is formed of plastic and being relatively rigid is provided to hold in position and accommodate within its bore 52 the tubular structure constituted by the tubing 40. The tube 50 includes two end portions 54 and 56. The end portions 58 and 60 of the tubular structure 40 extend outwardly of the ends 54 and 56 and are rolled backwardly therealong in order to form a coupling between the two components 40 and 50 as a consequence of which a unit is formed which can be easily handled and manipulated during assembly procedures. It will be noted that the tube 40 is a one piece monolithic structure to which detachable clips 48 are applied. The tube 50 is also a monolithic structure which provides a skeleton or support for the tube 40.

To house the aforegoing unit, there is provided a hub or housing 62 provided with first and second channels 64 and 66. The first channel is of larger diameter than the channel 66 thereby to define therebetween a shoulder 68. A catheter or needle arrangement such as, for example, the catheter 26 has an end portion 70 which is accommodated in the second channel 66. The unit formed by the tube 40 mounted on the tube 50 is accommodated in the first channel 64 and is in abutting relationship with the shoulder 60. A tapered joint plug 72 fits into the channel 64 and is of such a length as to sandwich the afore-described unit against the shoulder 68 to lock the same firmly in position. It will be noted that the plug 72 has a tapered passageway 74 which along with the passageway 76 of end portion 70 of catheter 26, for example, constitutes a continuous passageway with the passageway indicated at 78 relative to the aforesaid tubular structure. The plug 72 is friction welded in position or is otherwise fixed in locking position by bonding means of conventional type suitable for use in conjunction with intravenous procedures. The diameter of the tubular structure and the unit in which it performs is such that the same fits snugly within the channel 64 thereby to assure that fluid flowing through the illustrated structure passes through passageways 74, 78, and 76 in sequence.

Figure 3:
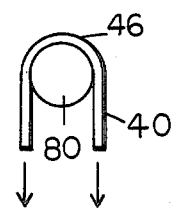
FIG. 3 is a diagrammatic view illustrating a procedural step in the manufacture of the arrangement of FIG. 2.
Figure 4:
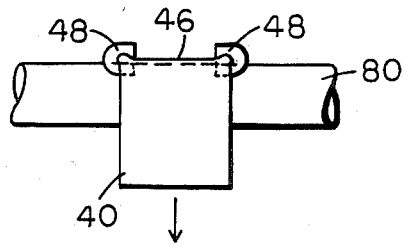
FIG. 4 is a side view corresponding to the illustration in FIG. 3.

FIGS. 3 and 4 illustrate the forming of the flattened section 46 mentioned hereinabove. To assist in forming this flattened portion, there is utilized a cylindrical rod or mandrel 80. The tube 40 is bent around this mandrel thereby forming the flattened portion on top of the mandrel. To hold the flattened portion in the flattened shape, there are employed the aforementioned clips 48. These clips engage no more than about 5% to 25% of the width of the tube thereby to leave a central portion in flattened position through which fluid may flow under the normal pressure of an intravenous procedure. These clips remain in position in the assembled and installed device, but may be readily removed therefrom for purposes of servicing or substitution or the like. The flattened portion provides a throat constriction which operates generally in the manner shown in FIGS. 5 and 6.

Figure 5:
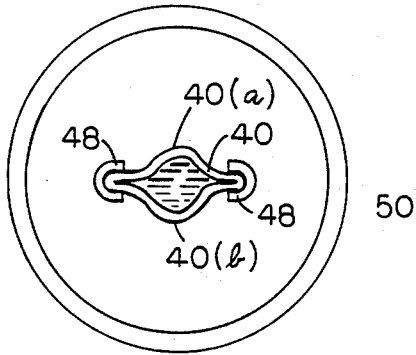
FIG. 5 is a diagrammatic view illustrating the operation of the arrangement of FIG. 2 with fluid flow permitted.
Figure 6:
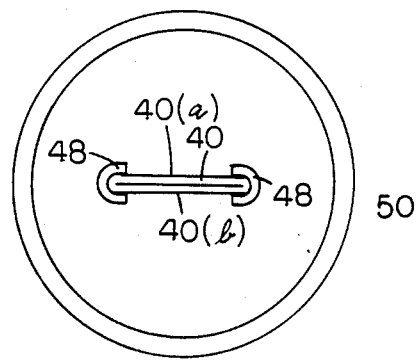
FIG. 6 is a view corresponding to FIG. 5 with flow terminated upon an opening of the system to ambient atmosphere.

With reference to FIGS. 5 and 6, there appears in these Figs. the support tube 50 and the operative tubular structure 40 as well as clips 48, all of this structure being diagrammatically shown in order to establish an explanation of the operation of the system. In FIG. 5, normal fluid pressure exerted by the pump 20 referred to hereinabove, forces fluid through the tube 40 and between the normally flat faces 40(a) and 40(b) thereof. Since the tube is formed of rubber and since the upstream section 42 tapers downwardly towards this section, the flow of fluid will not be impeded. During this time, clips 48 tend to hold the central portion 46 in flattened condition but in a yieldable manner so that this yieldable constraint will permit the deformation illustrated in FIG. 5 due to the pressure exerted by the pump 20 or even due to the force of gravity acting on the fluid in a system wherein the pump 20 is not employed.

In FIG. 6 is illustrated the situation where, for example, the pump 20 is not operating or the catheter 26 has become detached from the pump 20 and is opened to ambient atmosphere. In this case, the relative negative pressure in the vascular system as compared with ambient atmosphere causes a suction to be applied to the central portion 46 of the tubular structure 40 thereby to cause a sucking of the faces 40(a) and 40(b) together thereby to form a lock against the penetration of air thereby to prevent air bubbles from being sucked into the vascular system and thereby to insure against the formation of air embolisms or the like in the vascular system as might cause serious harm to the patient being treated.

While one such system has been described in detail relative to the catheter 26 connected downstream of the pump 20 and connected to the needle or catheter N as appears in FIG. 1, it should be noted that in accordance with the invention, more than one such safety arrangement might be employed. Thus, for example, it would be preferred in accordance with the invention if a second such safety arrangement would be provided, for example, in the catheter 18 at position 22 thereby to prevent the sucking of air into the pump 20 thereby to perform in the same manner as has been indicated hereinabove with respect to FIGS. 5 and 6.

It will now appear that there is provided in accordance with the invention, a flow control or safety arrangement comprising input and output means constituted by sections 42 and 44 each provided with a bore constituting a flow channel and further means such as the coupling section 46 adapted for providing a connecting channel between the bores in response to a positive pressure in one of the bores and for collapsing and thereby obturating the connecting channel in response to a pressure in one of said bores which is negative relative to ambient atmospheric pressure. The aforesaid input, output and further means constitute part of a tubular structure as has been described, this tubular structure preferably being monolithic and of a resilient material such as silicone rubber or the like.

In accordance with the invention, there is provided a clip arrangement which is mounted on the central portion of the tubular structure and whereby the tubular structure has a portion thereof yieldably constrained to a flattened shape. A relatively rigid support tube having spaced ends is provided with a bore within which the tubular structure is partly accommodated. The tubular structure includes end portions extending out of the support tube and being rolled back along the support tube ends for engagement therewith.

There will now be obvious to those skilled in the art many modifications and variations of the structure and manufacturing techniques described above. Such modifications and variations will not depart from the scope of the invention if defined by the following claims.

What is claimed is:

1. An intravenous system comprising a source of intravenous fluid, first catheter means for insertion into the vascular system of a patient, a pump for performing a pumping operation and urging the fluid from said source to said first catheter means, second catheter means coupling said pump to said source, said pump including means to terminate said pumping operation upon an opening of said second catheter means to ambient atmosphere, and the flow control device in at least said first catheter means to prevent movement of air therethrough upon an opening of the said first catheter means to ambient atmosphere.

2. An intravenous system of claim 1 wherein the tubular structure is of a resilient material.

3. An intravenous system as of claim 1 further comprising clip means and wherein the part of the tubular structure constituting said further means is yieldably constrained to flattened shape by said clip means.

4. An intravenous system of claim 1 wherein the tubular structure is of silicone rubber.

5. An intravenous system of claim 1 wherein the flow control means is in said catheter means for insertion into the vascular system of a patient, downstream of said pump.

6. A flow control device comprising:
   a tubular structure including input means and output means, each provided with a bore constituting a flow channel, and
   further means located between the bores of said input and output means of said tubular structure and having an open and a closed position, said further means providing for a connecting channel between said bores when said further means is in the open position, said further means normally being prestressed to said closed position and being forceable to said open position in response to a positive fluid pressure in the bore of said input means, said further means being constructed and arranged so as to return to said closed position and to obturate the connecting channel in response to a removal of positive fluid pressure from the bore of said input means and a pressure in the bore of said output means which is negative;
   a relatively rigid support tube having spaced ends and provided with a bore within which said tubular structure is partly accommodated, said tubular structure including end portions extending out of the support tube and being rolled over the support tube ends for engagement therewith; and
   a housing which is closed with respect to the surrounding environment provided with first and second channels of different diameters in coaxial relation to define a shoulder therebetween, said support tube and tubular structure insertable into said first channel and trapping said support tube and tubular structure against said shoulder and a catheter accommodated in said second channel, said plug means and catheter providing passageways coupled through said tubular structure.

7. A flow control device of claim 6 wherein the tubular structure is monolithic.

8. A flow control device of claim 6 wherein the tubular structure is of a resilient material.

9. A flow control device of claim 6 further comprising clip means and wherein the part of the tubular structure constituting said further means is yieldably constrained to flattened shape by said clip means.

10. A flow control device of claim 6 wherein the input and output means taper towards the said further means.

11. A flow control device of claim 6 wherein the tubular structure is of silicone rubber.

12. A flow control device of claim 6 further comprising a needle coupled to said catheter and adapted for insertion into the vascular system of a patient.

13. A flow control device comprising:
    a tubular structure having input means and output means, each provided with an open bore, channel means connecting said input and output bores and operating between open and closed positions, and
    clip means for retaining a portion of the channel means in a prestressed condition to obturate said channel means so as to maintain the channel means in said closed position; said channel means being forceable to said open position in response to a positive pressure in either one of said bores to facilitate flow through said channel means from the bore containing the positive pressure to the other bore, said flow control device capable of passing fluid in either direction depending upon which bore contains the positive pressure; said clip means returning said channel means to said closed position when said positive pressure is removed.

14. The flow control device of claim 13 wherein said channel means comprises a tubular structure of a resilient material.

15. The flow control device of claim 13 wherein said obturating means comprises clip means for retaining a portion of said flexible tubular structure in a flattened condition.

16. The flow control device of claim 13 further comprising a relatively rigid support member having spaced ends and provided with a bore within which said channel means is partly accommodated, said channel means further including end positions extending out of the support member and being rolled back along the support member ends for engagement therewith.

17. A flow control device comprising:

(a) input means and output means, each provided with a bore constituting a flow channel;

(b) further means comprising
 channel means connecting said input and output bores and operating between open and closed positions, and
 means to obturate said channel means so as to prestress and normally maintain the channel means in said closed position; said channel means being forceable to said open position in response to a positive pressure in one of said bores to facilitate flow therethrough; said obturating means returning said channel means to said closed position when said positive pressure is removed;

(c) a relatively rigid support member having spaced ends and provided with a bore within which said channel means is partly accommodated, said channel means including end portions extending out of the support member and being rolled over the support member ends for engagement therewith;

(d) a housing is closed with respect to the surrounding environment provided with first and second channels of different diameters in coaxial relation to define a shoulder therebetween; said support member and channel means being accommodated in said first channel;

(e) plug means insertable into said first channel and trapping said support member and channel means against said shoulder; and (f) a fluid directing member accommodated in said second channel, said plug means and fluid directing member providing passageways coupled through said channel means.

18. The flow control device of claim 17 wherein said fluid directing member is a catheter; said channel means is a tubular structure; and said support means is a relatively rigid support tube.

19. The flow control device of claim 18 further comprising a needle coupled to said catheter and adapted for insertion into the vascular system of a patient.

20. An intravenous system comprising a source of intravenous fluid, first catheter means for insertion into the vascular system of a patient, a pump for performing a pumping operation and urging the fluid from said source to said first catheter means, second catheter means coupling said pump to said source, said pump including means to terminate said pumping operation upon an opening of said second catheter means to ambient atmosphere, and flow control means in at least said first catheter means to prevent movement of air therethrough upon an opening of the said first catheter means to ambient atmosphere, said flow control means comprising:

a tubular structure having input means and output means, each provided with an open bore, channel means connecting said input and output bores and operating between open and closed positions; and clip means for retaining a portion of the channel means in a prestressed condition to obturate said channel means so as to maintain the channel means in said closed position; said channel means being forceable to said open position in response to a positive fluid pressure in either one of said bores to facilitate fluid flow through said channel means from the bore containing the positive pressure to the other bore, said flow control means capable of passing fluid in either direction depending upon which bore contains the positive pressure; said clip means returning said channel means to said closed position when said positive pressure is removed.

21. An intravenous system comprising a source of intravenous fluid, catheter means for insertion into the vascular system of a patient, pumping means for urging said fluid from said source to said catheter, fluid directing means connecting said source to said pump and further to said catheter means to facilitate delivery of said fluid to said patient, and flow control means located at least in said catheter means to prevent the introduction of air into the vascular system of the patient upon an opening of said catheter to ambient atmosphere, said flow control means comprising the flow control device of claim 13.

22. An intravenous system comprising a source of intravenous fluid, catheter means for insertion into the vascular system of a patient, pumping means for urging said fluid from said source to said catheter, fluid directing means connecting said source to said pump and further to said catheter means to facilitate delivery of said fluid to said patient, and flow control means located at least in said catheter means to prevent the introduction of air into the vascular system of the patient upon an opening of said catheter to ambient atmosphere, said flow control means comprising the flow control device of claim 17.

23. The intravenous system of claim 20 wherein said input, output and channel means comprises a tubular structure.

24. The intravenous system of claim 23 wherein said tubular structure comprises a resilient silicon rubber tube.

25. The intravenous system of claim 20 wherein said input and output means taper toward said further means.

26. A flow control device comprising:
tubular means having open input and output bores connected by channel means and operable between an open position to allow fluid flow therethrough and a closed position to prevent ambient pressure air from passing therethrough; and obturating means operatively associated with said channel means for prestressing and maintaining a portion of said channel means in said closed position, said channel means being forceable to said open position in response to a positive fluid pressure in said input or output bore of said tubular means through said channel means from the bore containing the positive pressure to the other bore, said flow control means capable of passing fluid in either direction depending upon which bore contains the positive fluid pressure; said obturating means returning said channel means to said closed position in response to a removal of said positive fluid pressure from said input or output bore.

27. The device of claim 26 further comprising a relatively rigid support member having spaced ends and an internal bore within which said tubular means is at least partly accommodated, said input and output bores of said tubular means including end portions extending out of the support member and being rolled over the support member ends for engagement therewith.

28. The device of claim 27 further comprising:
a housing provided with first and second channels of different diameters in coaxial relation to define a shoulder therebetween said support member and channel means, and being accommodated in said first channel, and plug means insertable into said first channel and trapping said support member and channel means against said shoulder.

29. The device of claim 28 wherein said obturating means comprises clip means for retaining said channel means portion in a closed condition in the absence of positive fluid pressure.

30. An intravenous system comprising a source of intravenous fluid, first catheter means for insertion into the vascular system of a patient, a pump for performing a pumping operation and urging the fluid from said source to said first catheter means, second catheter means coupling said pump to said source, said pump including means to terminate said pumping operation upon an opening of said second catheter means to ambient atmosphere, and flow control means in at least said first catheter means to prevent movement of air therethrough upon an opening of the said first catheter means to ambient atmosphere, said flow control means comprising the flow control device of claim 26.

* * * * *